United States Patent [19]

Nakane

[11] Patent Number: 4,607,048
[45] Date of Patent: Aug. 19, 1986

[54] 7-OXABICYCLOHEPTANE SUBSTITUTED ARYL AMINO PROSTAGLANDIN ANALOGS AND THEIR USE IN INHIBITING PLATELET AGGREGATION AND BRONCHOCONSTRICTION

[75] Inventor: Masami Nakane, Hopewell, N.J.

[73] Assignee: E. R. Squibb & Sons, Inc., Princeton, N.J.

[21] Appl. No.: 734,507

[22] Filed: May 16, 1985

[51] Int. Cl.$^4$ ................ A61K 31/335; A61K 31/557; C07D 307/00
[52] U.S. Cl. ................................... 514/469; 549/463
[58] Field of Search .................... 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,456,617 | 6/1984 | Nakane et al. | 549/463 |

FOREIGN PATENT DOCUMENTS 0043292 8/1982 European Pat. Off.
2039909 8/1980 United Kingdom.

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted aryl amino prostaglandin analogs are provided having the structural formula

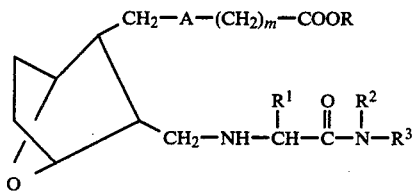

wherein A is $-CH=CH-$ or $-(CH_2)_2-$; m is 1 to 8; n is 1 to 5; R is H, lower alkyl, alkali metal or a polyhydroxyamino salt; $R^1$ is H, lower alkyl, hydroxyalkyl or aryl; $R^2$ is H, lower alkyl, aryl or cycloalkyl, $R^3$ is substituted aryl wherein the aryl group (which may be phenyl or naphthyl) is substituted with one or two of the following groups: hydroxy,

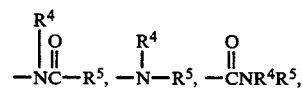

$SR^4$, $-CN$, $-NO_2$,

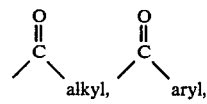

wherein $R^4$ and $R^5$ may be the same or different and are H or lower alkyl, and including all stereoisomers thereof.

The compounds are cardiovascular agents useful, for example, in the treatment of thrombotic disease.

12 Claims, No Drawings

6
7-OXABICYCLOHEPTANE SUBSTITUTED ARYL AMINO PROSTAGLANDIN ANALOGS AND THEIR USE IN INHIBITING PLATELET AGGREGATION AND BRONCHOCONSTRICTION

DESCRIPTION OF THE INVENTION

The present invention relates to 7-oxabicycloheptane substituted aryl amino prostaglandin analogs which are cardiovascular agents useful, for example, in the treatment of thrombotic disease. These compounds have the structural formula

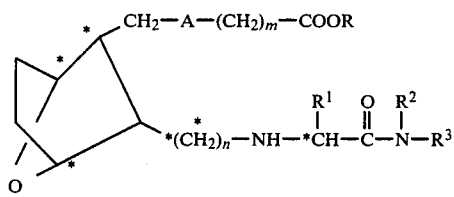

and including all stereoisomers thereof, wherein A is CH=CH or $(CH_2)_2$; m is 1 to 8; n is 1 to 5; R is H, lower alkyl, alkali metal or a protonated polyhydroxyamine such as tri(hydroxymethyl)amino methane or glucamine; $R^1$ is hydrogen, lower alkyl, hydroxyalkyl or aryl; $R^2$ is hydrogen, lower alkyl, aryl or cycloalkyl; and $R^3$ is substituted aryl or substituted arylalkyl wherein the aryl is substituted with one or two hydroxy,

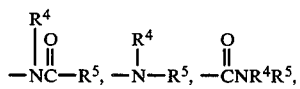

$SR^4$, —CN, $NO_2$ or

groups, wherein $R^4$ and $R^5$ may be the same or different and may be H or lower alkyl and $R^6$ is alkyl or aryl. The aryl substituent may be substituted at the ortho, meta or para position, with the para position being preferred.

Thus, the compounds of the invention may be encompassed by the following formulae:

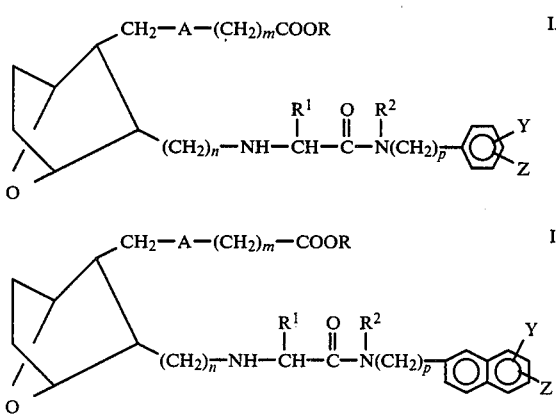

wherein p is 0 to 5, Y and Z may be the same or different and represent H, hydroxy,

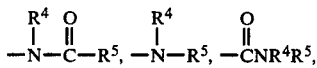

$SR^4$, —CN, $—NO_2$ or

with at least one of Y and Z being other than H.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups substituted with halo, such as F, Br, Cl or I or $CF_3$, alkoxy; hydroxy; alkylamino; alkanoylamino; arylcarbonylamino; nitro; cyano; thiol; alkylthio; aryl; alkyl-aryl; haloaryl; cycloalkyl; or alkylcycloalkyl.

The term "cycloalkyl" as employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups; 1 or 2 aryl groups; 1 or 2 halogens (Cl, Br, F or $CF_3$); 1 or 2 lower alkoxy groups; 1 or 2 hydroxyl groups; 1 or 2 $NR^4R^5$ groups; 1 or 2

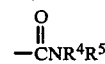

groups; 1 or 2

groups; 1 or 2 $SR^4$ groups; 1 or 2 nitro groups, 1 or 2 cyano groups, and/or 1 or 2 alkanoyl groups.

The term "aralkyl", "aryl-alkyl", "aryl-lower alkyl" or "cycloalkylalkyl" as used herein by itself or as part of another group refers to lower alkyl groups as discussed above having an aryl substituent, such as benzyl, or a cycloalkyl substituent.

The term "halogen" or "halo" as used herein by itself or as part of another group refers to chlorine, bromine, fluorine or iodine with chlorine being preferred.

The terms "$(CH_2)_m$", "$(CH_2)_n$" and "$(CH_2)_p$" include a straight or branched chain radicals having from 1 to 8 carbons in the normal chain in the case of "$(CH_2)_m$" and 1 to 5 carbons in the normal chain in the case of "$(CH_2)_n$" and "$(CH_2)_p$" and may contain one or more lower alkyl or halo substituents. Examples of $(CH_2)_m$, $(CH_2)_n''$ and $(CH_2)_p$ groups include $CH_2$, $CH_2CH_2$, $(CH_2)_3$, $(CH_2)_4$,

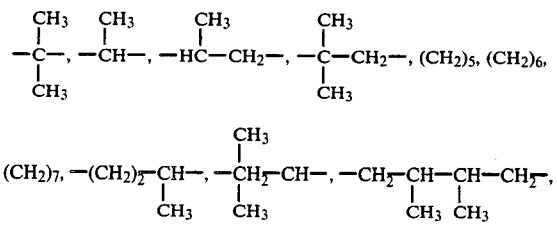

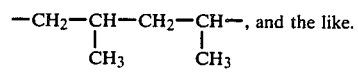, and the like.

Preferred are those compounds of formula I wherein A is $(CH_2)_2$ or $CH=CH$, m is 2 to 4, R is H, n is 1, and $R^1$ is hydrogen or lower alkyl, $R^2$ is hydrogen, $R^3$ is phenyl substituted with hydroxy at the para position and p is 0.

The various compounds of the invention may be prepared as outlined below.

A.

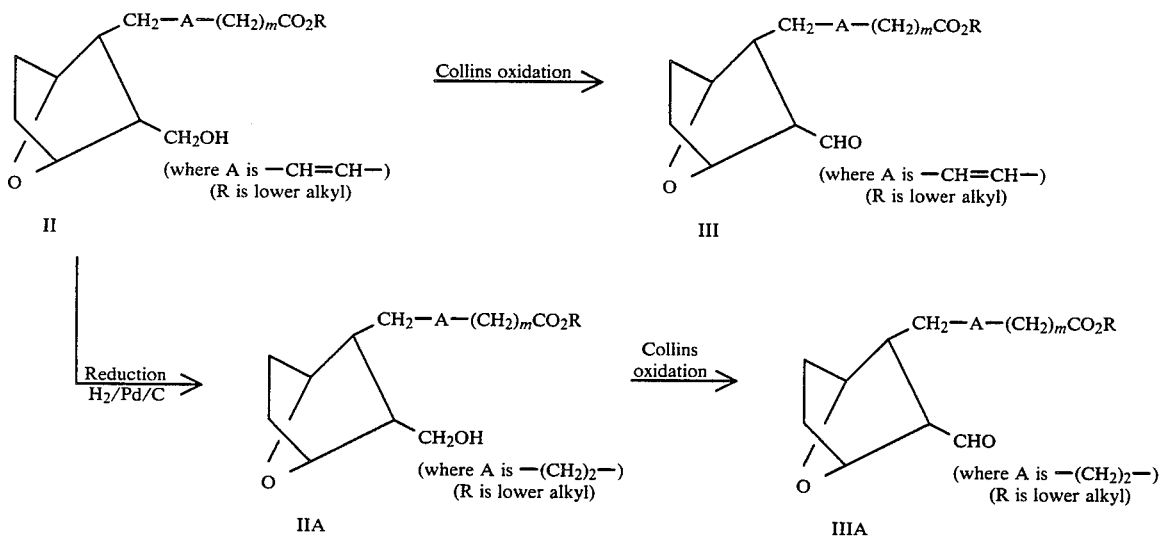

B. Where n is 1

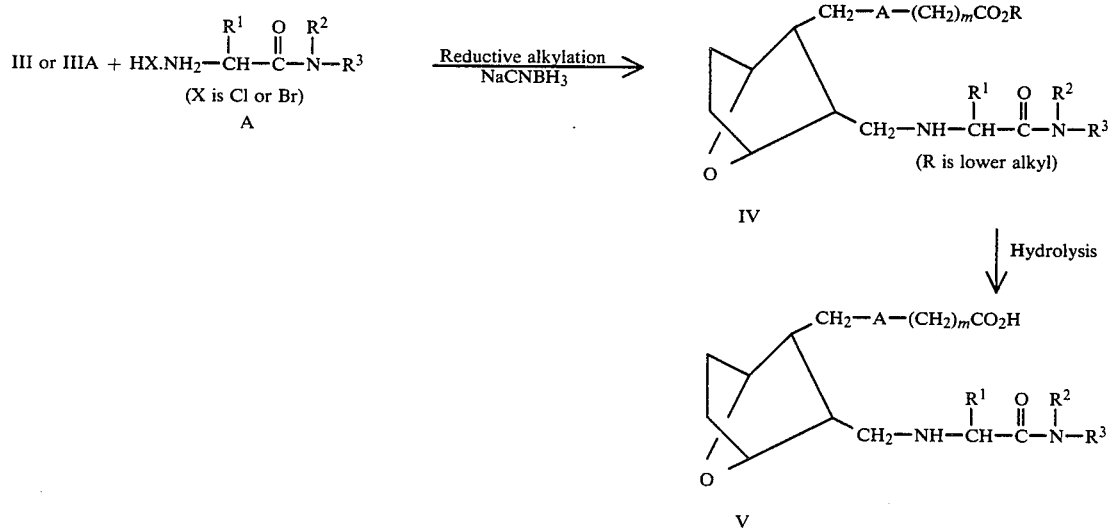

C. Where n is 2 to 5

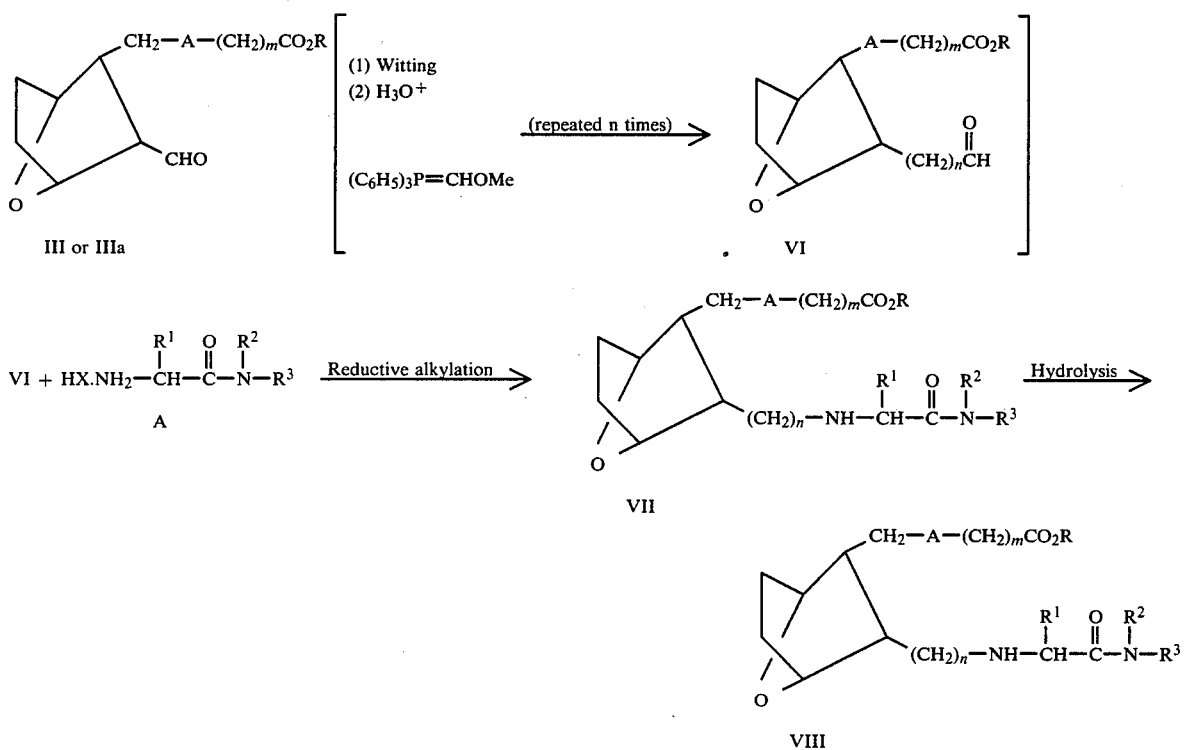

In the reaction sequence identified as "A", the starting lower alkyl ester containing the hydroxymethyl group, that is, compound II, (prepared as described in U.S. Pat. No. 4,143,054) is used to form the aldehyde III (where A is —CH=CH—) or IIIA (where A is (CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$), compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$).

As seen in reaction sequence "B", compounds of the invention where n is 1 that is

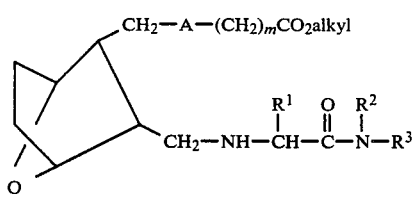

are prepared by reacting aldehyde III or IIIA with an amine of the structure

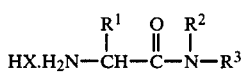

(wherein X is a halogen) employing a molar ratio of III or IIIA:amine A of within the range of from about 0.8:1 to about 1:1, in a solvent such as methanol or ethanol and a reducing agent such as sodium borohydride or sodium cyanoborohydride.

The reaction sequence identified as "C" is employed to prepare the compounds of the invention where n is 2 to 5, that is,

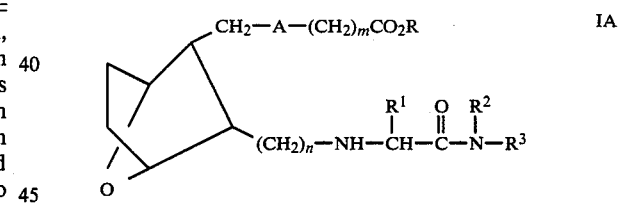

(where n is 2 to 5).

The aldehyde III or IIIA is used to prepare aldehyde VI (where n is 2-5) by carrying out a homologation sequence, such as a Wittig reaction with (C$_6$H$_5$)$_3$P=CHOMe followed by hydrolysis, (n−1) times. The aldehyde VI (where n=2-5) is thus carried on to the compounds of this invention where n is 2-5, that is

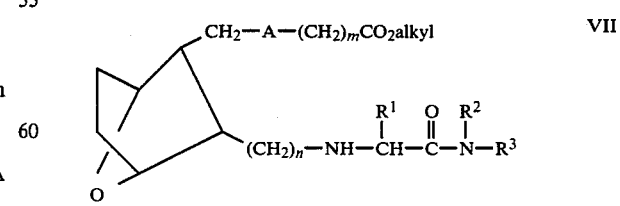

by reductive amination employing an amine of structure A in a weight ratio of VI:A of within the range of from about 0.8:1 to about 1:1 and a reducing agent such as sodium borohydride or sodium cyanoborohydride in a solvent such as methanol or ethanol and in the presence of acetic acid to form the compound of structure VII.

The esters IV and VII can be converted to the free acid, that is, to

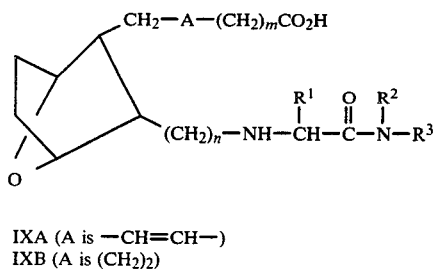

IXA (A is —CH=CH—)
IXB (A is (CH₂)₂)

by treating the esters with a base, such as lithium hydroxide, followed by neutralization with an acid, such as dilute hydrochloric acid or oxalic acid.

The starting amine salt of structure A, that is

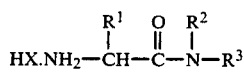   A may be prepared by reacting a solution of a protected amino acid of the structure B

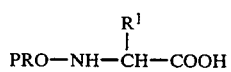   B (wherein the amine protecting group PRO is t-butyloxycarbonyl, benzyloxycarbonyl, phthalyl, o-nitrophenylsulfenyl, tosyl and the like) in a solvent such as tetrahydrofuran with a condensing agent, such as carbonyldiimidazole and an amine of the structure C

   C to form the protected amine of the structure D

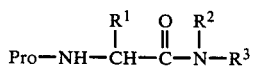   D

The protecting group (PRO) is removed from the formula D compound by reacting same with a strong acid such as trifluoroacetic acid, and hydrochloric acid or other appropriate reagent to form the amine salt A.

The compounds of this invention have four or five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting material and following the procedures as outlined in U.S. Pat. Nos. 4,143,054 and 4,456,617. Examples of such stereoisomers are set out below.

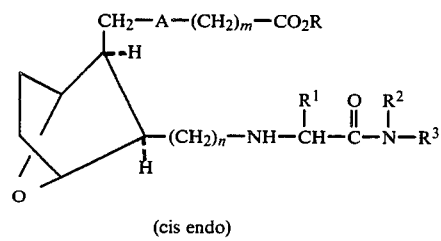

(cis endo)

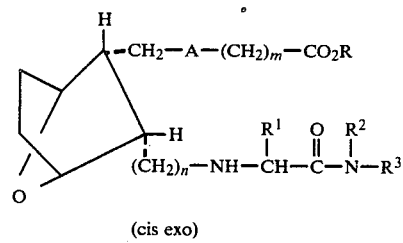

(cis exo)

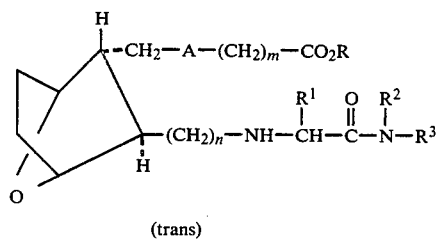

(trans)

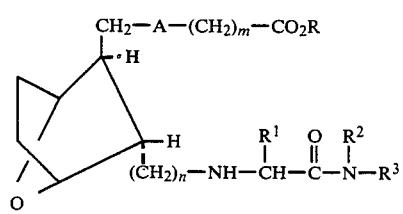

(trans)

The nucleus in each of the compounds of the invention depicted as

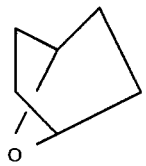

for matter of convenience; it will also be appreciated that the nucleus in the compounds of the invention may be depicted as

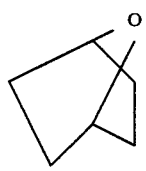

The compounds of this invetnion are cardiovascular agents useful as platelet aggregation inhibitors, such as in inhibiting arachidonic acid-induced platelet aggregation, e.g., for treatment of thrombotic disease such as coronary or cerebral thromboses, and inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of this invention.

EXAMPLE 1

[1S-[1β, 2α(5Z),3α,4β]]-7-[3-[[[2-[(4-Hydroxyphenyl)amino]-2-oxoethyl]amino]methyl]-7-oxabicyclo[2.2.1]-hept-2-yl]-5-heptenoic acid, methyl ester A. 2-(t-Butoxycarbonyl)amino-N-(4-hydroxyphenyl)acetamide t-Butyloxycarbonyl glycine (1.05 g, 6 mmol) was dissolved in distilled THF (50 ml) in an argon atmosphere. After cooling to 0° C., carbonyldiimidazole (CDI) (0.973 g, 6 mmol) was added and the mixture was stirred cold for 1 hour. p-Aminophenol (1.3 g, 12 mmol) and distilled Et$_3$N (2.5 ml ~18 mmol) were added and the mixture was allowed to warm slowly to room temperature and left stirring overnight. Most of the solvent was removed in vacuo. Chloroform (35 ml) was added. This was washed with 1N HCl solution (2×25 ml) and saturated NaCl solution (25 ml), dried (MgSO$_4$) and freed of solvent in vacuo leaving a tan solid (780 mg). This was triturated with a diisopropyl ether (IPE)-Et$_2$O mixture. The near white solid was harvested by filtration and dried to give title compound (554 mg, 34.7%). m.p. 152°-154° C.

TLC: Silica gel, EtOAc, UV+PMA R$_f$=0.62.

B. 2-Amino-N-(4-hydroxyphenyl)acetamide, hydrochloride

Compound from Part A (842 mg, 3.17 mmol) was cooled in an ice bath and treated with precooled distilled trifluoroacetic acid (TFA) (5 ml). The mixture was stirred at 0° C. for 50 minutes. Most of the TFA was removed in vacuo. Benzene was added and removed in vacuo. The residue was dissolved in MeOH and concentrated HCl (0.5 ml) was added. The methanol was removed in vacuo. Methanol was added twice and removed in vacuo leaving a solid. This was triturated with ether. The solid was harvested by filtration and washed with more ether leaving title amine·HCl (quant. yield) which was characterized by NMR.

C. [1S-[1β, 2α(5Z),3α,4β]]-7-[3-[[[2-[(4-Hydroxyphenyl)amino]-2-oxoethyl]amino]methyl]-7-oxabicyclo[2.2.1]hept-2-yl]-5-heptanoic acid, methyl ester

[1S-[1β,2α(5Z),3α,4β]]-7-[3-Formyl-7-oxabicyclo[2.2.1]hept-2-yl]-5-heptonic acid, methyl ester (prepared as described in U.S. Pat. No. 4,456,617) (532 mg, 2 mmol) was dissolved in MeOH (20 ml). Sodium acetate (197 mg, 2.4 mmol), Part B amine·HCl (486 mg, 2.4 mmol) and NaCNBH$_3$ (126 mg, 2.0 mmol) were added. The mixture was cooled in an ice bath and acetic acid (3.5 ml) was added dropwise. The ice bath was removed and the mixture was stirred for 3.5 hours, then acidified to pH 1 with 1N HCl. After stirring at room temperature 1 hour, a small amount of water was added and the mixture was basified by adding solid NaHCO$_3$. The product was extracted into EtOAc (3×50 ml), washed with saturated NaCl solution (25 ml), dried (MgSO$_4$) and freed of solvent in vacuo leaving very viscous material (805 mg). This was chromatographed on silica gel (60 g, Baker for flash chromatography), eluting with 4% MeOH in CH$_2$Cl$_2$ to give title methyl ester product as very viscous material (535 mg, 64.2%).

TLC: Silica gel, 10% MeOH in CH$_2$Cl$_2$, UV+vanillin R$_f$=0.49.

EXAMPLE 2

[1S-[1β, 2α(5Z),3α,4β]]-7-[3-[[[2-[(4-Hydroxyphenyl)amino]-2-oxoethyl]amino]methyl]-7-oxabicyclo[2.2.1]-hept-2-yl]-5-heptenoic acid Example 1 methyl ester (530 mg, 1.27 mmol) was dissolved in distilled THF (50 ml) and H$_2$O (10 ml) in an argon atmosphere, and the solution was treated with 1N LiOH (12 ml) and stirred at room temperature 1.5 hours. 1N HCl (12 ml) was added followed by solid KCl. The layers were separated and the aqueous layer was reextracted with EtOAc (3×50 ml). The combined organic layers were washed with saturated NaCl solution (25 ml), dried (MgSO$_4$) and freed of solvent in vacuo leaving a yellowish solid (398 mg, 77.8%). This was recrystallized from acetonitrile (~110 ml) to give title acid product (286.6 mg, 56%) as a white crystalline material. m.p. 176°-179° C.

Anal Calcd for C$_{22}$H$_{30}$O$_5$N$_2$: C, 65.65; H, 7.51; N, 6.96 Found: C, 65.48; H, 7.57; N, 6.90

TLC: Silica gel, 20% MeOH in CH$_2$Cl$_2$+HOAc (2 drops/10 ml), UV+vanillin, R$_f$=0.25

[α]$_D$=+0.4 (c=0.48 in MeOH).

EXAMPLE 3

[1β, 2α(5Z),3α,4β]-7-[3-[[[2-[4-(Acetylamino)phenyl]amino]-2-oxoethyl]amino]methyl]-7-oxabicyclo[2.2.1]hept-2-yl]-5-heptenoic acid, methyl ester A. N-[4-[[N-(t-BOC)-Glycyl]amino]phenyl]-acetamide A solution of N-(t-butyloxycarbonyl)-glycine (4.38 g, 25 mmol) in dry THF (100 ml) is cooled to 0° C. in an argon atmosphere. Carbonyl diimidazole (CDI) (4.1 g, 25 mmol) is added and the mixture was stirred at 0° for 1 hour. 4-(Acetylamino)-aniline (4.1 g, 27.5 mmol) is then added and the mixture is allowed to warm slowly to room temperature and left stirring overnight. The solvent is removed in vacuo. The residue is dissolved in CH$_2$Cl$_2$ (100 ml) and washed with 10% KHSO$_4$ solution (100 ml), saturated NaHCO₃ solution (100 ml) and H₂O (100 ml). After drying (MgSO₄), the solvent is removed in vacuo leaving a crude product. This sample is purified to give the title A compound.

B. 2-Amino-N-(4-phenyl)acetamide hydrochloride-acetamide hydrochloride

The t-BOC derivative prepared in Part A (3.5 g, 114 mmol) is treated with cold (0°) distilled trifluoroacetic acid in an argon atmosphere. The solution is stirred at 0° C. for 50 minutes. The trifluoroacetic acid is removed in vacuo and benzene is added and removed in vacuo. The residue is dissolved in methanol and an excess of concentrated HCl solution is added. This solution is taken to dryness in vacuo. Twice ethanol is added and removed in vacuo leaving the title B hydrochloride.

C. [1β, 2α(5Z),3α,4β]-7-[3-[[[2-[4-(Acetylamino)-phenyl]amino]-2-oxoethyl]amino]methyl]-7-oxabicyclo[2.2.1]hept-2-yl]-5-heptenoic acid, methyl ester

[1β,2α(5Z),3α,4β]-7-[3-Formyl-7-oxabicyclo[2.2.1-]hept-2-yl]-5-heptenoic acid, methyl ester (532 mg, 2 mmol) is dissolved in methanol (20 ml) in an argon atmosphere. Sodium acetate (197 mg, 2.4 mmol) is added followed by the Part B hydrochloride (584 mg, 2.4 mmol) and NaCNBH₃ (126 mg, 2.0 mmol). After cooling in an ice bath, acetic acid (3.5 ml) is added dropwise. The cooling bath is removed and the mixture is stirred at room temperature 5 hours. 1N HCl solution is added to pH 1 and stirring was continued 45 minutes. A small amount of water is added and the mixture is basified with solid NaHCO₃. The product is extracted into ethyl acetate (3×50 ml). The combined extracts are washed with saturated NaCl solution (50 ml), dried (MgSO₄) and freed of solvent in vacuo leaving a viscous oil. This is chromatographed on silica gel (70 g) eluting with 2% MeOH in CH₂Cl₂ to give the title methyl ester as an oil (437.5 mg).

EXAMPLE 4

[1β,2α(5Z),3α,4β]-7-[3-[[[2-[4-(Acetylamino)phenyl]-amino]-2-oxoethyl]amino]methyl]-7-oxabicyclo[2.2.1]-hept-2-yl]-5-heptenoic acid The Example 3 methyl ester (0.78 mmol) is dissolved in THF (30 ml) and water (5 ml) in an argon atmosphere. 1N LiOH solution (7.8 ml) is added and the mixture is stirred at room temperature 5 hours, After neutralizing with 1N HCl solution (7.8 ml), the solution is saturated with NaCl. The layers are separated and the aqueous is re-extracted with ethyl acetate (3×50 ml). The combined organic layers are dried (MgSO₄) and freed of solvent in vacuo leaving a viscous oil. This is chromatographed twice on SiliCAR CC-7 (25 g each time) eluting with 2–10% MeOH in CH₂Cl₂ to give the title acid product.

EXAMPLE 5

[1β,2α(5Z),3α,4β]-7-[3-[[[2-[(4-Nitrophenyl)-amino]-2-oxoethyl]amino]methyl]-7-oxabicyclo[2.2.1]-hept-2-yl]-5-heptenoic acid, methyl ester A. 2-Amino-N-(4-nitrophenyl)acetamide The title compound is prepared according to H. Tuppy, U. Wiesbauer, and E. Wintersberger, Z. Physiol. Chem., (1962) 329 278–288.

B. [1β,2α(5Z),3α,4β]-7-[3-[[[2-[(4-Nitrophenyl)amino]-2-oxoethyl]amino]-methyl]-7-oxabicyclo]2.2.1]hept-2-yl]-5-heptenoic acid, methyl ester

[1β,2α(5Z),3α,4β]-7-[3-Formyl-7-oxabicyclo-[2.2.1]hept-2-yl]-5-heptenoic acid, methyl ester (532 mg, 2 mmol) is dissolved in methanol (20 ml) in an argon atmosphere. Title A amide (429 mg, 2.2 mmol) and NaCNBH₃ (126 mg, 2 mmol) are added. After cooling in an ice bath, HOAc (3.5 ml) is added dropwise. The cooling bath is removed and the mixture is stirred 3 hours at room temperature. 1N HCl solution is added to pH 1 and stirring is continued 45 minutes. A small amount of water is added and the mixture is basified with solid NaHCO₃. The product is extracted into ethyl acetate (3×50 ml). The combined extracts are washed with NaCl solution (50 ml), dried (MgSO₄) and freed of solvent in vacuo. The residue is chromatographed on silica gel 60 to give title methyl ester compound.

EXAMPLE 6

[1β,2α(5Z),3α,4β]-7-[3-[[[2-[(4-Nitrophenyl)-amino]-2-oxoethyl]amino]methyl]-7-oxabicyclo-[2.2.1]-hept-2-yl]-5-heptenoic acid The Example 5 methyl ester (476 mg, 1.07 mmole) is dissolved in THF (50 ml) and water (9 ml) in an argon atmosphere. 1N LiOH solution (10.7 ml) is added and the mixture is stirred at room temperature 3.5 hours. After adding 1N HCl solution (10.7 ml, pH∼5) the mixture is poured into saturated NaCl solution (200 ml). This is extracted with EtOAc (3×100 ml). The combined extracts are washed with saturated NaCl solution, dried over MgSO₄ and freed of solvent giving a crude product which is purified by silica gel chromatography to give the title compound.

EXAMPLE 7

[1β,2α(5Z),3α,4β]-7-[3-[[[2-[4-(Ethylthio)phenyl-)amino]-2-oxoethyl]amino]methyl]-7-oxabicyclo[2.2.1-]hept-2-yl]-5-heptenoic acid, methyl ester A. 2-(t-BOC)amino-N-[4-(ethylthio)phenyl]acetamide t-BOC glycine (2.62 g, 15 mmol) is dissolved in distilled THF (100 ml) in an argon atmosphere. The solution is cooled in an ice bath and carbonyl diimidazole (CDI) (2.43 g, 15 mmol) is added. After stirring at 0° for 1 hour, 4-(ethylthio)aniline (2.30 g, 15 mmol) is added. The mixture is allowed to warm slowly to room temperature and is left stirring overnight. The solvent is removed in vacuo and CHCl₃ (75 ml) is added. The solution is washed with 1N HCl (2×50 ml), saturated NaHCO₃ (50 ml), saturated NaCl solution (50 ml) and dried (MgSO₄). The solvent is removed in vacuo leaving a solid. This is purified to give the title compound.

B. 2-Amino-N-[4-(ethylthio)phenyl]acetamide hydrochloride

Part A compound (2.77 g, 8.9 mmol) is cooled in an ice bath in an argon atmosphere and treated with precooled distilled TFA (15 ml). The solution is cooled at 0° C. for 1 hour. The TFA is removed in vacuo. Benzene is added once and removed in vacuo. The residue is dissolved in MeOH and treated with concentrated HCl (1.5 ml). The solvent is removed in vacuo and methanol is added twice and removed in vacuo leaving a solid. This is triturated with Et₂O, harvested by filtration and dried in vacuo to give the title compound.

C. [1β,2α(5Z),3α,4β]-7-[3-[[[2-[4-(Ethylthio)phenyl]amino]-2-oxoethyl]aminio]methyl]-7-oxabicyclo[2.2.1]hept-2-yl]-5-heptenoic acid, methyl ester

[1β,2α(5Z),3α,4β]-7-[3-Formyl-7-oxabicyclo-[2.2.1]hept-2-yl]-5-heptenoic acid, methyl ester (532 mg, 2 mmol) is dissolved in methanol (20 ml) in an argon atmosphere. Sodium acetate (197 mg, 2.4 mmol), Part B amine hydrochloride (591 mg, 2.4 mmol) and NaCNBH₃ (126 mg, 2.0 mmol) are added. The mixture is cooled in an ice bath and acetic acid (3.5 ml) is added dropwise. The cooling bath is removed and the mixture is left stirring overnight at room temperature. The mixture is acidified to pH 1 with 1N HCl solution and stirred at room temperature 1 hour. Water (~10 ml) is added and the mixture is basified by adding solid NaHCO₃ solution. The proudct is extracted into CHCl₃ (3×50 ml). The combined extracts are washed with saturated NaCl solution (25 ml), dried (MgSO₄) and freed of solvent in vacuo leaving an oil (985 mg). This is chromatographed on silica gel to give the title compound.

EXAMPLE 8

[1β,2α(5Z),3α,4β]-7-[3-[[[2-[[4-(Ethylthio)phenyl]amino]-2-oxoethyl]amino]methyl]-7-oxabicyclo[2.2.1-]hept-2-yl]-5-heptenoic acid Part C methyl ester (681 mg, 1.48 mmol) is dissolved in distilled THF (70 ml) and water (12 ml) in an argon atmosphere and treated with 1N LiOH solution (14 ml). After stirring at room temperature 5½ hours, the mixture is acidified to pH~2 by adding 1N HCl solution (~15 ml). Solid KCl is added and the layers are separated. The aqueous layer is reextracted with EtOAc (3×50 ml). The combined organic layers are washed with saturated NaCl solution (25 ml), dried (MgSO₄) and freed of solvent in vacuo leaving very viscous material. This is purified to give the title compound.

EXAMPLE 9

(1β,2β,3α,4β)-7-[3-[[[2-[(4-Hydroxyphenyl)]amino]-2-oxoethyl]amino]methyl]-7-oxabicyclo[2.2.1]hept-2-yl]heptanoic acid A. (1β,2β,3β,4β)-7-[3-(Hydroxymethyl)-7-oxabicylco[2.2.1]hept-2-yl]heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. (1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anhydrous CH₂Cl₂ was added, under an argon atmosphere, 730 mg (2.8 mmole) of the title A alcohol in 2 ml of CH₂Cl₂. The reaction was stirred for 2 hours at 25°, diluted with 100 ml of ether, filtered through a pad of florisil, and evaporated to furnish 670 mg (88%) of the title B compound as a white crystalline solid.

C. (1β,2β,3α,4β)-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate and concentrated to afford 765.0 mg (98%) of the title C aldehyde.

D. (1β,2β,3α,4β)-7-[3-[[[2-[(4-Hydroxyphenyl)amino]-2-oxoethyl]amino]methyl]-7-oxabicyclo[2.2.1]hept-2-yl]heptanoic acid Following the procedure of Example 1, except substituting the Part C aldehyde for the aldehyde used in Example 1 Part C, the title product is obtained.

EXAMPLE 10

[1β,2α(5Z),3β,4β]-7-[3-[[[2-[(4-Hydroxyphenyl)amino]-2-oxoethyl]amino]methyl]-7-oxabicyclo[2.2.1-]hept-2-yl]-5-heptenoic acid, methyl ester A. [1β,2α(5Z),3β,4β]-7-[3-Formyl-7-oxabicyclo[2.2.1-]hept-2-yl]-5-heptenoic acid, methyl ester A solution of pyridine (14.6 ml) in dichloromethane (500 ml) was treated portionwise with chromium trioxide (9.06 g) with vigorous stirring. After addition was complete, the mixture was stirred at room temperature for 30 minutes, then treated with celite (30 g) and then with [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (25 ml). The reaction mixture was stirred at room temperature for 30 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether, and filtered through a pad of Baker silica gel, washed with ether and the filtrate taken to dryness in vacuo leaving 3.79 g (92%) of pale yellow oil.

B. [1β,2α(5Z),3β,4β]-7-[3-[[[2-[(4-Hydroxyphenyl)amino]-2-oxoethyl]methyl]-7-oxabicyclo[2.2.1]hept-2-yl]-5-heptenoic acid, methyl ester Part A aldehyde (532 mg, 2 mmol) is dissolved in methanol (20 ml) in an argon atmosphere. Sodium acetate (197 mg, 2.4 mmol) is added followed by the Example 1 Part B amine hydrochloride (448 mg, 2.4 mmol) and NaCNBH₂ (126 mg, 2.0 mmol). After cooling in an ice bath, acetic acid (3.5 ml) is added dropwise. The cooling bath is removed and the mixture is stirred at room temperature 5 hours. 1N HCl solution is added to pH 1 and stirring is continued 45 minutes. A small amount of water is added and the mixture is basified with solid NaHCO₃. The product is extracted into ethyl acetate (3×50 ml). The combined extracts are washed with saturated NaCl solution (50 ml), dried (MgSO₄) and freed of solvent in vacuo leaving a viscous oil. This is chromatographed on silica gel 60 (70 g) eluting with 2% MeOH in CH₂Cl₂ to give the title methyl ester.

EXAMPLE 11

[1β,2α(5Z),3β,4β]-7-[3-[[2-[(4-Hydroxyphenyl)amino]-2-oxoethyl]amino]methyl]-7-oxabicyclo[2.2.1-]hept-2-yl]-5-heptenoic acid Following the procedure of Example 2 except substituting methyl ester of Example 10 for methyl ester of Example 1, the title compound is obtained.

EXAMPLE 12

[1β,2α(5Z),3α,4β]-7-[3-[[[2-[(4-Hydroxyphenyl)amino]-1-methyl-2-oxoethyl]amino]methyl]-7-oxabicyclo[2.2.1]hept-2-yl]-5-heptenoic acid Following the procedure of Examples 1 and 2 except substituting t-BOC-alanine for the protected glycine, the title compound is obtained.

EXAMPLE 13

[1β,2α(5Z),3α,4β]-7-[3-[[[2-[[(4-Acetylamino)phenyl]amino]-1-(2-methylpropyl)-2-oxoethyl]amino]methyl]-7-oxabicyclo[2.2.1]hept-2-yl]-5-heptenoic acid Following the procedure of Examples 3 and 4 except substituting t-BOC-leucine for the protected glycine, the title compound is obtained.

EXAMPLE 14

(1β,2β,3α,4β)-7-[3-[[[2-[(4-Hydroxyphenyl)amino]-1-(1-methylethyl)-2-oxoethyl]amino]methyl]-7-oxabicyclo[2.2.1]hept-2-yl]heptanoic acid Following the procedure of Example 9 except substituting t-BOC-valine for the protected glycine, the title compound is obtained.

EXAMPLE 15

[1β,2α(5Z),3α,4β]-7-[3-[[[2-[(4-Nitrophenyl)amino]-1-benzyl-2-oxoethyl]amino]methyl]-7-oxabicyclo[2.2.1]hept-2-yl]-5-heptenoic acid Following the procedure of Examples 5 and 6 except substituting t-BOC-phenylalanine for the protected glycine, the title compound is obtained.

EXAMPLE 16

[1β,2α(5Z),3α,4β]-7-[3-[[[2-[[4-(Ethylthio)phenyl]amino]-1-hydroxymethyl-2-oxoethyl]amino]methyl]-7-oxabicyclo[2.2.1]hept-2-yl]-5-heptenoic acid Following the procedure of Examples 7 and 8 except substituting t-BOC-serine for the protected glycine, the title compound is obtained.

EXAMPLE 17

[1β,2α(5Z),3α,4β]-7-[3-[[[2-[(2-Hydroxyphenyl)amino]-2-oxoethyl]amino]methyl]-7-oxabicyclo[2.2.1]hept-2-yl]-5-heptenoic acid, hydrochloride salt A. 2-(t-Butoxycarbonyl)amino-N-(2-hydroxyphenyl)acetamide t-BOC-glycine (2.62 g, 15 mmol) was dissolved in distilled THF (100 ml) in an argon atmosphere. After cooling in an ice bath, CDI (2.43 g, 15 mmol) was added and the mixture was stirred cold for 1 hour. o-Aminophenol (3.2%, 30 mmol which had been recrystallized from H₂O) and distilled Et₃N (6.3 ml ~45 mmol) were added and the mixture was allowed to warm slowly to room temperature and left stirring overnight. Most of the solvent was removed in vacuo. The residue was dissolved in CHCl₃ (75 ml) and washed with 1N HCl solution (2×50 ml) and saturated NaCl solution (1×50 ml), dried (MgSO₄) and freed of solvent in vacuo leaving reddish crystalline material (2.913 g). This was recrystallized from CH₃CN (~10 ml) to give the title compound as nearly colorless crystals 2.04 g (51%), m.p. 155°-158° C. TLC: silica gel, 5% MeOH in CH₂Cl₂, UV+PMA, R$_f$=0.41.

B. 2-Amino-N-(2-hydroxyphenyl)acetamide

Part A compound (1.96 g, 7.37 mmol), under argon, was cooled in an ice bath and treated with precooled distilled TFA (10 ml). The mixture was stirred at 0° for 50 minutes and the TFA was then removed in vacuo. Benzene was added once and removed in vacuo. The residue was dissolved in MeOH and treated with concentrated HCl (1.0 ml). The solvent was removed in vacuo. Twice MeOH was added and removed in vacuo leaving a white solid. This was triturated with Et₂O and harvested by filtration to give 1.57 g (quant) of title compound.

C. [1S-[1β,2α(5Z),3α,4β]]-7-[3-[[[2-[(2-Hydroxyphenyl)amino]-2-oxoethyl]amino]methyl]-7-oxabicyclo[2.2.1]hept-2-yl]-5-heptenoic acid, methyl ester

[1S-[1β,2α(5Z),3α,4β]]-7-[3-Formyl-7-oxabicyclo[2.2.1]hept-2-yl]-5-heptenoic acid, methyl ester (532 mg, 2 mmol) was dissovled in MeOH (20 ml) in an argon atmosphere. Sodium acetate (197 mg, 2.4 mmol), part B compound (486 mg, 2.4 mmole) and NaCNBH₃ (126 mg, 2.0 mmol) were added. The solution was cooled in an ice bath and HOAc (3.5 ml) was added dropwise. The mixture was left stirring overnight at room temperature. The mixture was acidified to pH 1 with 1N HCl solution and stirred at room temperature 1 hour. A small amount of water was added and the mixture was basified by adding solid NaHCO₃. The product was extracted into EtOAc (3×50 ml). The combined EtOAc extracts were washed with saturated NaCl solution (25 ml), dried (MgSO₄) and freed of solvent in vacuo leaving a white solid (842 mg). This was recrystallized from CH₃CN (12-15 ml) to give the title compound, 497 mg (60%), m.p. 129°-131° C. TLC: silica gel, 10% MeOH in CH₂Cl₂, UV+vanillin R$_f$=0.64.

D. [1S-[1β,2α(5Z),3α,4β]]-7-[3-[[[2-[(2-Hydroxyphenyl)amino]-2-oxoethyl]amino]methyl]-7-oxabicyclo[2.2.1]hept-2-yl]-5-heptenoic acid, hydrochloride salt Part C methyl ester (459 mg, 1.1 mmol) was dissolved in distilled THF (50 ml) and water (10 ml) in an argon atmosphere. The solution was treated with 1N LiOH solution (11 ml) and stirred at room temperature 2½ hours. The mixture was then acidified to pH~2 with 1N HCl solution (12 ml). Saturated KCl was added and the layers were separated. The aqueous layer was reextracted with 10% THF in EtOAc (3×50 ml). The combined organic layers were washed with saturated KCl solution (15 ml), dried (MgSO₄) and freed of solvent in vacuo leaving a white solid (301 mg). The MgSO₄ filter cake was washed with warm THF (50 ml) to give additional white solid (88 mg) identical to the first material by TLC. The combined solids were recrystallized for isopropyl alcohol to give the title compound (302 mg, 62.5%), m.p. 194°-196° C.

Anal Calcd for $C_{22}H_{30}O_5N_2 \cdot HCl$: C, 60.20; H, 7.12; N, 6.38; Cl, 8.08. Found: C, 60.20; H, 7.13; N, 6.37; Cl, 8.09.

TLC: silica gel, 20% MeOH in CH₂Cl₂, UV+vanillin R$_f$=0.59.

[α]$_D$= +2.4° (c=1, MeOH)

EXAMPLE 18

[1S-[1β,2α(5Z),3α,4β]]-7-[3-[[[2-[(3-Hydroxyphenyl)amino]-2-oxoethyl]amino]methyl]-7-oxabicyclo[2.2.1]hept-2-yl]-5-heptenoic acid, hydrochloride salt A. 2-(t-Butoxylcarbonyl)amino-N-(3-hydroxyphenyl)acetamide t-BOC glycine (2.62 g, 15 mmol) was dissolved in distilled THF (100 ml) in an argon atmosphere. After cooling to 0° C., CDI (2.43 g, 15 mmol) was added and the mixture was stirred cold for 1 hour. m-Amino phenol (3.27 g, 30 mmol, recrystallized from toluene) and distilled Et₃N (6.3 ml, 45 mmol) were added. The mixture was allowed to warm slowly to room temperature and left stirring overnight. The solvent was removed in vacuo. The residue was dissolved in CHCl₃ (75 ml) and washed with 1N HCl solution (2×50 ml) and saturated NaCl solution (50 ml), dried (MgSO₄), and freed of solvent in vacuo leaving a tan foam. This was chromatographed on silica gel (60 g, Baker for flash chromatography) eluting with 2% MeOH in CH₂Cl₂ to give the product as a white foam (1.42 g, 35.6%), TLC: silica gel, 5% MeOH in CH₂Cl₂, UV+vanillin R$_f$=0.31.

B. 2-Amino-N-(3-hydroxyphenyl)acetamide, hydrochloride salt

Part A compound (1.34 g, 5.40 mmol) was cooled in an ice bath and treated with precooled distilled TFA (10 ml) in an argon atmosphere. The mixture was stirred at 0° C. for 50 minutes. The TFA was removed in vacuo and benzene was added once and removed in vacuo. The residue was dissolved in MeOH and treated with 0.8 ml concentrated HCl. The solvent was removed in vacuo. Methanol was added twice and removed in vacuo leaving a white solid. This was triturated with ether and harvested by filtration to give the hydrochloride (0.97 g, 95%).

C. [1S-[1β,2α(5Z),3α,4β]]-7-[3-[[[2-[(3-Hydroxyphenyl)amino[-2-oxoethyl]amino]methyl]-7-oxabicyclo[2.2.1]hept-2-yl-5-heptenoic acid, methyl ester

[1S-[1β,2α(5Z),3α,4β]]-7-[3-Formyl-7-oxabicyclo[2.2.1]hept-2-yl-5-heptenoic acid, methyl ester (532 mg, 2 mmol) was dissolved in methanol (20 ml) in an argon atmosphere. Sodium acetate (197 mg, 2.4 mmol), part B compund (486 mg, 2.4 mmol) and NaCNBH₃ (126 mg, 2.0 mmol) were added. The solution was cooled in an ice bath and acetic acid (3.5 ml) was added dropwise. The mixture was left stirring overnight at room temperature. After acidifying to pH 1 with 1N HCl, the mixture was stirred at room temperature 1 hour. A small amount of water was added and the mixture was basified by adding solid NaHCO₃. The product was extracted into EtOAc (3×50 ml). The combined EtOAc extracts were washed with saturated NaCl solution (25 ml), dried (MgSO₄) and freed of solvent in vacuo leaving a very viscous oil (800 mg). This was chromatographed on silica gel (60 g, Baker for flash chromatography), eluting with 2.5 to 4% MeOH in CH₂Cl₂ to give the desired ester (580 mg, 69.6%) which became a waxy solid on standing. TLC: silica gel, 10% MeOH in CH₂Cl₂, UV+vanillin R$_f$=0.42.

D. [1S-[1β,2α(5Z),3α,4β]]-7-[3-[[[2-[(3-Hydroxyphenyl)amino]-2-oxoethyl]amino]methyl]-7-oxabicyclo[2.2.1]hept-2-yl]-5-heptenoic acid, hydrochloride salt Part C ester (491 mg, 1.18 mmol) was dissolved in distilled THF (50 ml) and water (10 ml) in an argon atmosphere. 1N LiOH solution (12 ml) was added and the mixture was stirred at room temperature 2 hours. The mixture was acidified to pH ~2 by adding 1N HCl solution (13 ml). Solid KCl was added and the layers were separated. The aqueous layer was reextracted with distilled THF (100 ml). The combined THF layers were washed with saturated KCl solution (15 ml), dried (MgSO₄) and freed of solvent in vacuo. Benzene was added and removed in vacuo. The residue was then dissolved in a mixture of methanol and benzene and taken to dryness in vacuo leaving a viscous foam (506 mg). This was crystallized from a mixture of ethyl acetate and methanol to give the title compound (374 mg, 71%), m.p. 106°–109° C. dec.

Anal Calcd for C$_{22}$H$_{30}$O$_5$N$_2$·HCl·0.3H$_2$O: C, 59.46; H, 7.17; N, 6.30; Cl, 7.98. Found: C, 59.45; H, 7.19; N, 6.20; Cl, 7.98.

[α]$_D$=+2.7° (c=1, MeOH)

TLC: Silica gel, 20% MeOH in CH$_2$Cl$_2$, UV+vanillin, R$_f$=0.37.

EXAMPLE 19

[1S-[1β,2α(5Z),3α,4β]]-7-[3-[[[2-[(3,5-Dihydroxyphenyl)amino]-2-oxoethyl]amino]methyl]-7-oxabicyclo[2.2.1]hept-2-yl]-5-heptenoic acid Following the procedure of Examples 1 and 2 except substituting 3,5-dihydroxyphenylamine for p-aminophenol, the title product is obtained.

EXAMPLE 20

[1β,2α(5Z),3α,4β]-7-[3-[[[2-[[3-(Propionylamino)phenyl]amino]-2-oxoethyl]amino]methyl]-7-oxabicyclo[2.2.1]hept-2-yl]-5-heptenoic acid Following the procedure of Examples 3 and 4 except substituting 3-(propionylamino)aniline for 4-(acetylamino)aniline, the title product is obtained.

EXAMPLE 21

[1β,2α(5Z),3α,4β]-7-[3-[[[2-[4-(Diethylamino)phenyl]amino]-2-oxoethyl]amino]methyl]-7-oxabicyclo[2.2.1]hept-2-yl]-5-heptenoic acid Following the procedure of Examples 5 and 6 except substituting 4-(diethylamino)aniline for 4-nitroaniline, the title product is obtained.

EXAMPLE 22

[1β,2α(5Z),3α,4β]-7-[3-[[[2-[[2-(Propylthio)phenyl]amino]-2-oxoethyl]amino]methyl]-7-oxabicyclo[2.2.1]hept-2-yl]-5-heptenoic acid.

Following the procedure of Examples 7 and 8 except substituting 2-(propylthio)aniline for 4-(ethylthio)aniline, the title product is obtained.

EXAMPLE 23

(1β,2α,3β,4β)-7-[3-[[[2-[[(3-Hydroxyphenyl)-2-oxoethyl]amino]methyl]-7-oxabicyclo[2.2.21]hept-2-yl]heptanoic acid.

Following the procedure of Example 9 except substituting 3-hydroxyaniline for 4-hydroxyaniline, the title product is obtained.

EXAMPLE 24

[1S-[1β,2α(5Z),3α,4β]]-7-[3-[[[2-[[(4-Hydroxyphenyl)-methyl]amino]-2-oxoethyl]amino]methyl]-7-oxabicyclo[2.2.1]hept-2-yl]-5-heptenoic acid Following the procedure of Examples 1 and 2 except substituting 4-hydroxybenzylamine for 4-hydroxyaniline, the title product is obtained.

EXAMPLE 25

[1S-[1β,2α(5Z),3α, 4β]]-7-[3-[[[2-[[2-(4-Hydroxyphenyl)ethyl]amino]-2-oxoethyl]amino]methyl]-7-oxabicyclo[2.2.1]hept-2-yl]-5-heptenoic acid Following the procedure of Examples 1 and 2 except substituting 2-(4-hydroxyphenyl)ethylamine for 4-hydroxyaniline, the title product is obtained.

It will also be appreciated that the compounds of the invention wherein m is any of 1 to 8 may be prepared as outlined above starting with hydroxymethyl compound II (wherein m is any of 1 to 8) which may be prepared as described in U.S. Pat. No. 4,143,054.

What is claimed is:

1. A compound having the structural formula

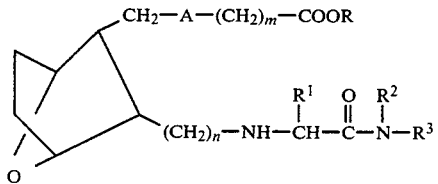

and including all stereoisomers thereof; wherein A is —CH=CH— or —(CH$_2$)$_2$—;
m is 1 to 8; n is 1 to 5;
R is hydrogen, lower lakyl, alkali metal or a polyhydroxylamine salt;
R$^1$ is hydrogen, lower alkyl, hydroxyalkyl or aryl;
R$^2$ is hydrogen, lower alkyl, aryl, or cycloalkyl; and
R$^3$ is substituted aryl or substituted arylalkyl wherein the aryl group is substituted with one or two of the following groups: hydroxy,

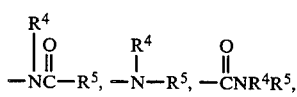

SR$^4$, —CN, —NO$_2$,

wherein R$^6$ is alkyl or aryl, wherein R$^4$ and R$^5$ may be the same or different and may be hydrogen or lower alkyl;
and wherein the term alkyl or lower alkyl by itself or as part of another group contains 1 to 12 carbons which may be unsubstituted or substituted with halo, CF$_3$, alkoxy, hydroxy, alkylamino, alkanoylamino, arylcarbonylamino, nitro, cyano, thiol, alkylthio, aryl, alkyl-aryl, haloaryl, cycloalkyl or alkylcycloalkyl; the term aryl by itself or as part of another group is phenyl or naphthyl and which ring unless otherwise indicated, may be unsubstituted or substituted with 1 or 2 halogens, 1 or 2 lower alkyl groups, 1 or 2 aryl groups, 1 or 2 lower alkoxy groups, 1 or 2 hydroxyls, 1 or 2 NR$^4$R$^5$ groups, 1 or 2

groups, 1 or 2 NR$^4$—CO—R$^5$ groups, 1 or 2 SR$^4$ groups, 1 or 2 nitro groups, 1 or 2 cyano groups and/or 1 or 2 alkanoyl groups; and the term cycloalkyl by itself or as part of another group contains 3 to 12 carbons and which may be unsubstituted or substituted with one or two halogens, one or two lower alkyl groups and/or one or two lower alkoxy groups; and (CH$_2$)$_m$ and (CH$_2$)$_n$ include straight or branched chain radicals having from 1 to 8 carbons in the normal chain in the case of (CH$_2$)$_m$, and 1 to 5 carbons in the normal chain in the case of (CH$_2$)$_n$ and may contain 1 or 2 lower alkyl or halo groups.

2. The compound as defined in claim 1 wherein R$^3$ is

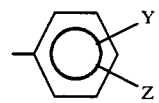

wherein Y and Z may be the same or different and are H, hydroxy,

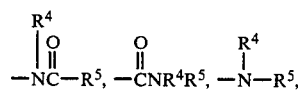

—SR$^4$, —CN, —NO$_2$,

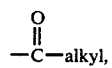

or aryl, with at least one of Y and Z being other than H.

3. The compound as defined in claim 2 wherein R$^3$ is

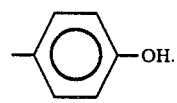

4. The compound as defined in claim 1 wherein R is H or CH$_3$.

5. The compound as defined in claim 1 wherein A is —CH=CH—.

6. The compound as defined in claim 1 wherein A is —CH=CH—, m is 2 to 4, n is 1, R is H or CH$_3$, R$^1$ is H, R$^2$ is H and R$^3$ is hydroxyphenyl.

7. The compound as defined in claim 1 wherein A is —CH=CH—, m is 3, n is 1, R is H, R$^1$ is H, R$^2$ is H and R$^3$ is p-hydroxy phenyl.

8. The compound as defined in claim 1 having the name [1S-[1β,2α(5Z),3α,4β]]-7-[3-[[[2-[(4-hydroxyphenyl)amino]-2-oxoethyl]amino]methyl]-7-oxabicyclo[2.2.1]-hept-2-yl]-5-heptenoic acid or its methyl ester and including all stereoisomers thereof.

9. A method of inhibiting arachidonic acid-induced platelet aggregation and bronochoconstriction, which comprises administering to the circulatory system of a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

11. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

12. A method of inhibiting platelet aggregation, inhibiting bronochoconstriction associated with asthma or treating peripheral vascular diseases, which comprises administering to a mammalian host an effective amount of a compound as defined in claim 1 or a pharmaceutically acceptable salt thereof.

* * * * *